United States Patent [19]
Falkenström

[11] Patent Number: 5,405,393
[45] Date of Patent: Apr. 11, 1995

[54] TEMPOROMANDIBULAR JOINT PROSTHESIS

[75] Inventor: Che Hsin Falkenström, Enschede, Netherlands

[73] Assignee: Academisch Ziekenhuis Groningen, Groningen, Netherlands

[21] Appl. No.: 78,979

[22] Filed: Jun. 16, 1993

[30] Foreign Application Priority Data

Jun. 2, 1993 [EP] European Pat. Off. ............ 93201583

[51] Int. Cl.⁶ .............................................. A61F 2/30
[52] U.S. Cl. .................................................... 623/18
[58] Field of Search ....................... 623/16, 18, 22, 23; 606/69–71

[56] References Cited

U.S. PATENT DOCUMENTS

| | | | |
|---|---|---|---|
| 3,488,779 | 1/1970 | Christensen | 623/18 |
| 4,693,722 | 9/1987 | Wall | 623/18 |
| 4,917,701 | 4/1990 | Morgan | 623/18 X |

FOREIGN PATENT DOCUMENTS

0203719 12/1986 European Pat. Off. .
2558721 8/1985 France .
WO87/04917 8/1987 WIPO .

OTHER PUBLICATIONS

Kent, John N. et a., "Temporomandibular Joint Condylar Prosthesis: A Ten-year Report", Journal of Oral Maxillofacial Surgery, vol. 41, pp. 245 through 254, 1983.

Kiehn, Clifford L. et al., "Total Prosthetic Replacement of the Temporomandibular Joint", Annals of Plastic Surgery, vol. 2, No. 1, Jan. 1979, pp. 5 through 15.

*Primary Examiner*—Randall L. Green
*Assistant Examiner*—Mary Beth O. Jones
*Attorney, Agent, or Firm*—Varnum, Riddering, Schmidt & Howlett

[57] ABSTRACT

A temporomandibular joint prosthesis comprising a cranial prosthesis-part comprising a support surface adapted to be seated against bone tissue in the area of and/or adjacent to the natural glenoid fossa and/or the articular eminence and a mandibular prosthesis-part adapted to be pivotable relative to the cranial prosthesis-part when in implanted condition. The mandibular prosthesis-part is pivotable about a center of rotation which is located in such a position relative to the support surface of the cranial prosthesis-part, that in implanted condition the center of rotation is located substantially inferior to the center of the natural mandibular condyle.

The prosthesis allows a natural combination of rotation and translation of the mandibular condyle in spite of the loss of the function of the lateral pterygoid muscles.

14 Claims, 3 Drawing Sheets

TEMPOROMANDIBULAR JOINT PROSTHESIS

FIELD OF THE INVENTION

The invention relates to a temporomandibular (jaw) joint prosthesis comprising a cranial (skull-side) prosthesis-part comprising a support surface adapted to be seated against bone tissue in the area of and/or adjacent to the natural glenoid fossa and/or the articular eminence and a mandibular (lower jaw-side) prosthesis-part adapted to be pivotable relative to the cranial prosthesis-part when in implanted condition.

BACKGROUND OF THE INVENTION

A treatment to counteract dysfunction of natural joints by causes such as ankylosis, osteoarthrosis, tumour or developmental disorders is to partially or completely replace the natural joint by a prosthesis.

For the treatment of dysfunctions of the temporomandibular joint, maxillofacial surgeons generally prefer a total temporomandibular joint prosthesis as identified in the preamble to preclude any risk of intrusion of the artificial condylar head into the midcranial fossa through the fossa roof or the possibility of condylar head resorption.

The natural temporomandibular joint allows both rotation and essentially horizontal translation of the mandibular condyle. Translation is controlled by lateral pterygoid muscles which are attached to the mandibular condyle. The function of these muscles is lost when the mandibular condyle to which they are attached is replaced by a mandibular prosthesis-part.

Examples of such a total temporomandibular joint prostheses are described in: 'Total Prosthetic Replacement of Temporomandibular Joint' by C. D. Kiehn et al. in Ann Plast Surg, 1979; 2:5 and in: 'Temporomandibular Joint Condylar Prosthesis: A Ten Year Report', by J. N. Kent et al. in Journal of Oral Maxillofacial Surgery,1983; 41:245-254 . In these and other known prostheses of this type, the anatomical shape of the natural articulating surfaces, i.e. the mandibular condyle, the articular eminence and the glenoid fossa, is essentially copied.

After implantation of a known prosthesis as discussed above, the mandible can only rotate about a fixed point at the side of the prosthesis, which point essentially corresponds with the centre of the replaced natural mandibular condyle, so instead of the muscular control of the translatory movement of the jaw a fixed point of rotation is obtained, precluding translatory movement of the mandible (lower jaw) at the side where the prosthesis is implanted.

This is uncomfortable for the patient and impairs the function of the mandible. Furthermore, rotation of the jaw about a substantially vertical axis is caused when a translation occurs in the opposite joint. This unnatural rotation causes exertion of abnormal loads on the opposite joint and thus an increased risk of dysfunction of the opposite natural joint. This is particularly undesirable when the prosthesis is implanted in a patient suffering from a disease which tends to affect the joints in general. Because of the above-described disadvantages of known temporomandibular joint prostheses, temporomandibular joint replacements are seldom performed in practice.

SUMMARY OF THE INVENTION

It is an object of the present invention to overcome these disadvantages by providing a temporomandibular joint prosthesis which provides a better user comfort and an improved function of the mandible, and allows a more natural mandibular motion.

According to the present invention, this object is achieved by providing a temporomandibular joint prosthesis of the above-described type in which the mandibular prosthesis-part is pivotable about a centre of rotation which is located in such a position relative to the support surface of the cranial prosthesis-parts that in implanted condition the centre of rotation is located substantially inferior to the centre of the natural mandibular condyle.

Due to these features, a more natural motion of the mandible, including translational movement of the prosthesis-portion located at the position of the replaced mandibular condyle, is obtained in spite of the loss of the function of the lateral pterygoid muscles.

The invention is based on the insight that to achieve the above-mentioned objects, the designer should primarily aim at restoration of the biomechanical functions of the joint, whereas hitherto designers were focused predominantly on providing an anatomical structure looking similar to the natural structure to be replaced.

The invention can also be embodied in a cranial prosthesis-part for use as part of a prosthesis according to a particular embodiment of the invention having a fixed centre of rotation of the mandibular prosthesis-part. This cranial prosthesis-part comprises a support surface adapted to be seated against bone tissue in the area of or adjacent to the natural glenoid fossa and/or the articular eminence, a sphere-shaped cavity or convex element, the centre defined by said sphere being located in such a substantially fixed position relative to the support surface, that in implanted condition said centre is located between 5 and 25 mm, and preferably about 15 mm, inferior to the centre of the natural mandibular condyle.

DETAILED DESCRIPTION OF A PREFERRED AND OTHER EMBODIMENTS OF THE INVENTION

Figure 1:
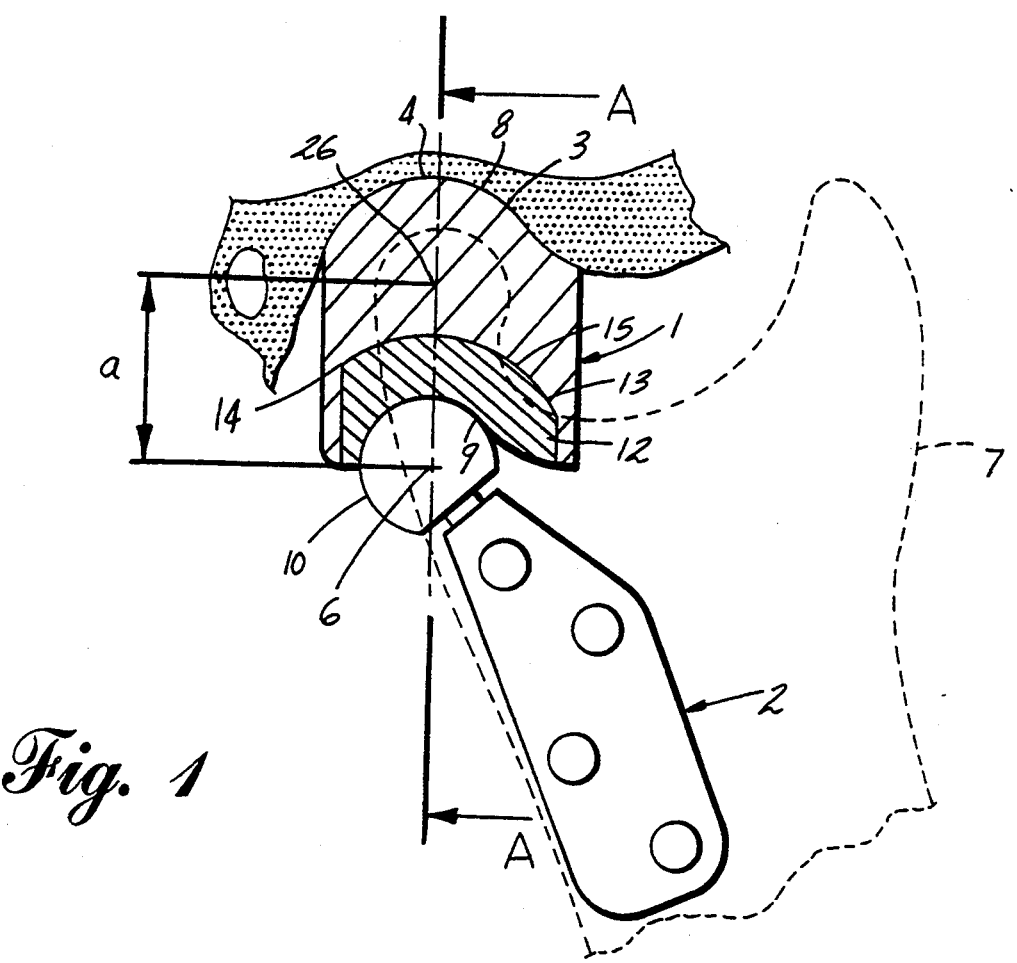
FIG. 1 is a side view in cross-section along the line B—B in FIG. 2 of an implanted right-side prosthesis according to the invention.

The invention will first be described with reference to the presently preferred embodiment shown in FIGS. 1 and 2. Subsequently the other embodiments shown in FIGS. 3-5 will be described and elucidated. Corresponding parts of the various embodiments are designated by identical reference numerals.

Figure 2:
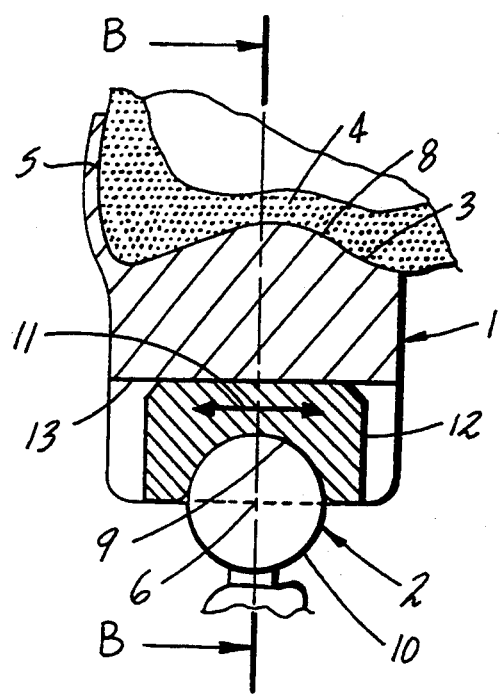
FIG. 2 is a side view in cross-section along the line A—A in FIG. 1.

In FIGS. 1 and 2 a temporomandibular joint prosthesis comprising a cranial prosthesis-part 1 and a mandibular prosthesis-part 2 is shown.

The cranial prosthesis-part may be provided with a support surface adapted and located to be fitted against a lateral side 5 of the zygomatic arch and/or the articular tubercle as is usual with known prostheses. The fossa prosthesis-part will then be supported mainly by bone screws anchored in the zygomatic arch and/or the articular tubercle. It is however preferred, to provide the cranial prosthesis-part 1, instead or in addition, with a support surface 3 adapted and located to be fitted to bone tissue 4 of the natural glenoid fossa and/or the articular eminence, so that an improved load distribution and support of the fossa prosthesis-part 1 is obtained. The support surface 3 shown in FIGS. 1 and 2 is fitted to both the glenoid fossa and a part of the articular eminence to obtain an optimal load distribution. The support surface 3 may be fitted to a large degree prior to implantation if the shape of the fossa is determined using for example computer tomography. The shape of the support surface 3 of a standard or customized prosthesis may be fitted or more accurately fitted using bone cement such as PMMA, which is however less bio-inert than suitable materials for manufacturing the cranial prosthesis-part.

The mandibular prosthesis-part 2 is adapted to be pivotable relative to the cranial prosthesis-part 1 about a centre of rotation 6 which is located in such a position relative to the support surface 3 of the cranial prosthesis-part 1, that in implanted condition the centre of rotation 6 is located substantially inferior to the centre 26 of the natural mandibular condyle.

This allows a natural motion of the mandible 7 including translational movement of the prosthesis 2 replacing the mandibular condyle in spite of the loss of the function of the lateral pterygoid muscles.

To achieve that in implanted condition the centre of rotation is located substantially inferior to the centre 26 of the natural mandibular condyle, in a prosthesis of which the support surface 3 of the cranial prosthesis-part 1 is adapted to be fitted to bone tissue 4 of the fossa, the centre of rotation 6 will be located in a plane parallel to and at a distance of more than 11 mm from a central portion 8 of that part of the support surface 3 of the cranial prosthesis-part 1. After implantation, this central portion 8 will be fitted to a central portion of the fossa. In addition, the support surface 3 may also be supported by other bone tissue, as is shown in the drawings.

The required distance between the central portion 8 of the support surface 3 and the plane to obtain a predetermined distance between the centre of the former natural mandibular condyle and the centre of rotation 6 may vary somewhat dependent from the morphology of the patient (in particular the depth of the fossa) and from the intended use of bone cement between the fossa prosthesis-part 1 and the bone tissue 4 of the fossa.

The most natural motion of the mandible 7 is obtained if the centre of rotation 6 is located in such a position relative to the support surface 3 of the cranial prosthesis-part 1, that in implanted condition that centre of rotation 6 is located between 5 and 60 mm inferior to the centre of the natural mandibular condyle.

To achieve this amount of inferior displacement of the centre of rotation 6 relative to the centre 26 of the natural mandibular condyle in a prosthesis of which the support surface 3 of the cranial prosthesis-part 1 is adapted to be fitted to bone tissue 4 of the fossa, the centre of rotation 6 will be located in a plane parallel to and at a distance of between 13 and 68 mm from a central portion 8 of the support surface 3 of the cranial prosthesis-part 1.

In the prosthesis shown in FIGS. 1 and 2, the mandibular prosthesis-part 2 is, at least in side-view, pivotable about a single centre of rotation 6. This is advantageous for obtaining a simple reliable construction with a long lifetime, in particular regarding wear, and requiring little space. For these reasons, presently a construction with a single centre of rotation is preferred over constructions in which an instantaneous centre of rotation moves along a path (centrode) when the mandible is articulated, although with the latter type of constructions (see FIGS. 3-5) a somewhat better reproduction of the motion of the mandible supported by a healthy, natural joint can be achieved.

For prostheses with a single centre of rotation 6 for obtaining an optimal fit of the motion of the mandible after implantation relative to the mandible articulated by a natural, healthy joint, the centre of rotation should preferably be located in such a position relative to the support surface 3 of the cranial prosthesis-part 1, that in implanted condition that centre of rotation 6 is located between 5 and 25 mm inferior to the centre of the natural mandibular condyle.

Best results regarding avoidance of rotation of the intercondylar axis in frontal and transversal planes, avoidance of mediolateral movement of the contralateral condyle and avoidance of overstretching of the temporomandibular ligament at the side of the prosthesis are generally achieved with single centre of rotation prostheses if the centre of rotation 6 is located 15 mm inferior to the centre of the natural mandibular condyle.

In combination with this inferior displacement, an anterior displacement of the centre of rotation 6 relative to the centre of the natural mandibular condyle of up to 5 mm and also a slight posterior displacement provides good results from a kinematic point of view.

To obtain the above-mentioned inferior displacements of 5 to 25 mm and preferably 15 mm in a prosthesis of which the support surface 3 is adapted to be fitted to bone tissue 4 of the fossa, the centre of rotation 6 is to be located in a plane parallel to and at a distance between 13 and 33 mm, respectively of about 23 mm, from a central portion 8 of the support surface 3 of the cranial prosthesis-part 1.

The cranial prosthesis-part 1 shown in FIGS. 1 and 2 comprises a sphere-shaped cavity 9 and the mandibular prosthesis-part 2 comprises a sphere-shaped convex element 10 adapted to be seated in the cavity 9 with a sliding fit. Thus the forces exerted on the joint are always well distributed over the bearing surfaces. This is of particular importance in a temporomandibular joint prosthesis, because of the important forces exerted thereon and the influence of surface pressure on wear of biologically suitable bearing materials, which was and still is a major concern in the field of artificial joint design. The radial clearance between the convex element 10 and the cavity 9 is preferably about 0.1 mm but dependent on the elasticity of the bearing material other amounts of clearance may be preferable.

It is noted, that in principle the convex element may also be provided on the cranial prosthesis-part and the concavity may also be provided on the mandibular prosthesis-part.

A problem which occurs when implanting a temporomandibular prosthesis is, that the prosthesis-parts have to be exactly positioned relative to each other to avoid a pretension in both the contralateral joint and the implanted, artificial joint, i.e. the distance between the skull-side and the mandible side bearing-surfaces of the joints should correspond exactly. Due to such pretensions, additional forces are exerted on the=temporomandibular joints causing additional wear and friction.

In the prosthesis shown in FIGS. 1 and 2, this problem is solved by adapting the prosthesis-parts 1 and 2 for translational displacement relative to each other in directions 11 which are oriented essentially medial and lateral when the prosthesis is in implanted condition. The exact direction of the allowed relative movements in implanted condition may be exactly lateral and medial, but also may be somewhat oblique, for example at an angle of 10°–20° to the tranversal plane.

Thus the prosthesis-parts are not mutually fixed in medial-lateral direction 11 and can adapt to their relative medial-lateral positions. Moreover, medial and lateral movement of the mandible is allowed, for example during chewing.

Since in the prosthesis shown in FIGS. 1 and 2 the centre of rotation 6 is displaced away from the glenoid fossa relative to the position of the centre of the natural mandibular condyle, sufficient room is present between the fossa and the sphere-shaped convex element 10 of the mandible condyle prosthesis-part 2 for a traveller 12 provided with the sphere-shaped cavity 9 or the sphere-shaped convex element 10 and a guide 13. The traveller 12 is movable along a guide 13 in the direction 11 of translational displacement. Thus a simple and reliable means of providing the desired medial and lateral translational movability is obtained.

The guide 13 is provided in form of a channel having a composite cross-section with, in implanted condition, a posterior edge and an anteriorly and upwardly facing rounded portion 15. The traveller is shaped correspondingly. Due to this shape, surface pressure is kept relatively low, by providing a maximum surface extending perpendicular to the major forces exerted on the joint.

The traveller 12 can for example be made from a suitable polymer such as UHMWPE. For the condyle for example Alumina ($A_2O_3$) would be suitable. For the basis of the cranial prosthesis-part 1 an Co—Cr—Mo alloy is preferred to keep wear low, although this material is less bio-inert than suitable titanium alloys. To alleviate this problem, the support surface 3 of the cranial prosthesis-part 1 may be covered with hydroxylapatite, which stimulates bone ingrowth. Screws and the stem of the mandibular prosthesis-part 2 are preferably made out of a titanium alloy.

The screws are preferably fixed in titanium implants with thread inside to avoid damage of the bone when the screws are screwed out in the event the prosthesis has to be removed for replacement or reconditioning. Such screw/implant combinations can also advantageously be used for anchoring other types of implants which sometimes have to be replaced or reconditioned.

Figure 3:
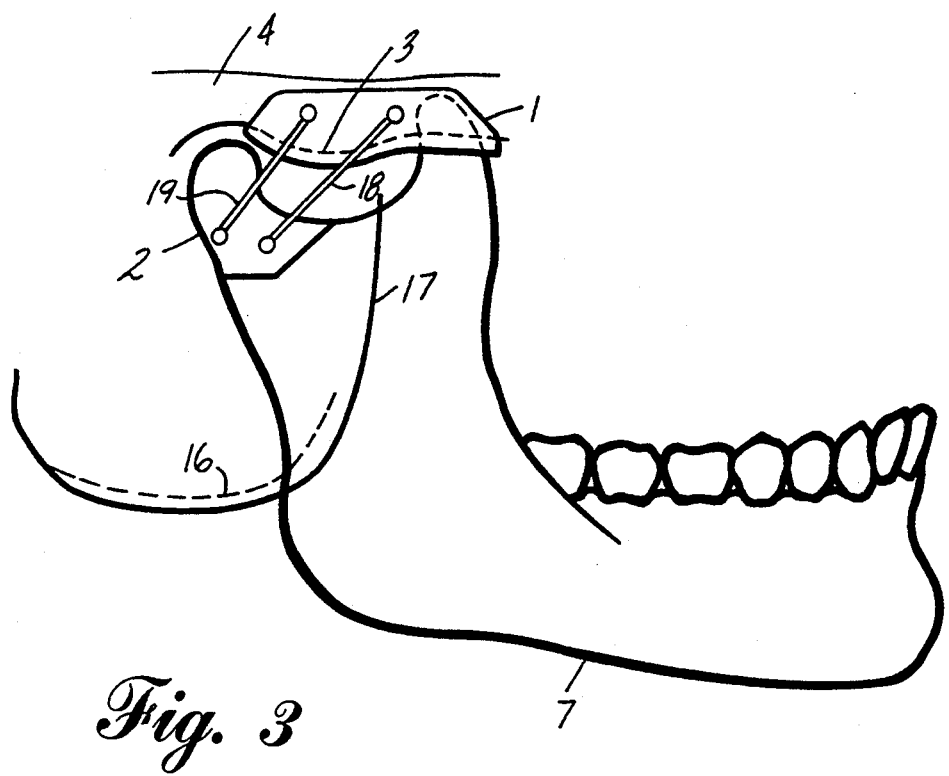
FIG. 3 is a schematical side view of a second implanted prosthesis according to the invention.
Figure 4:
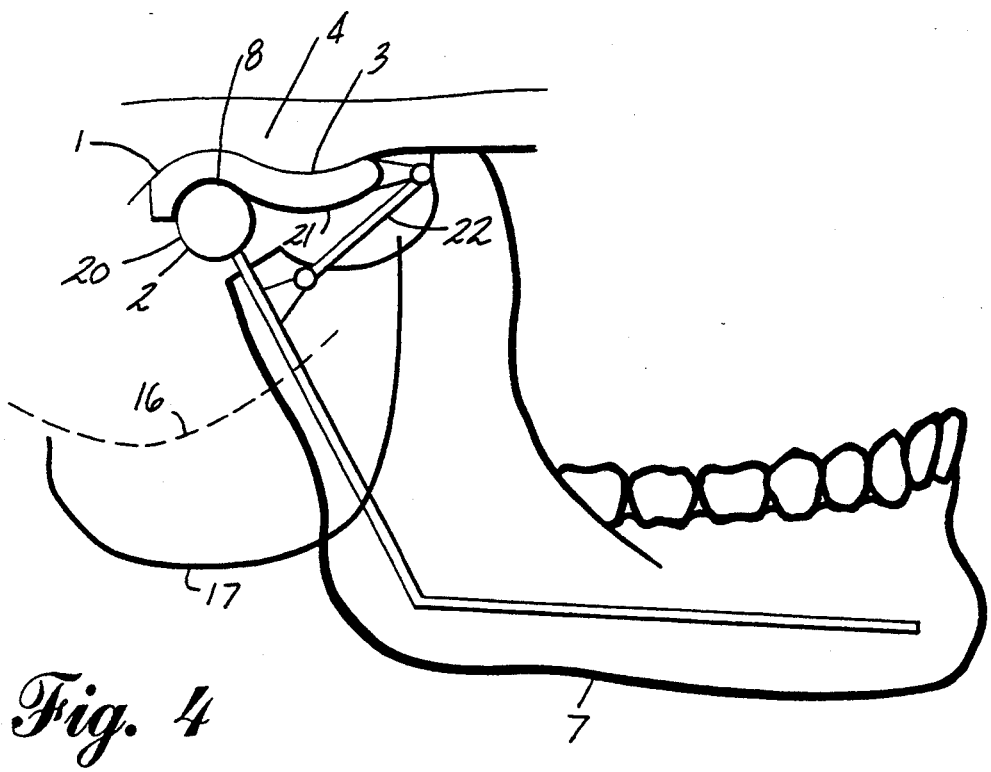
FIG. 4 is a schematical side view of a third implanted prosthesis according to the invention.
Figure 5:
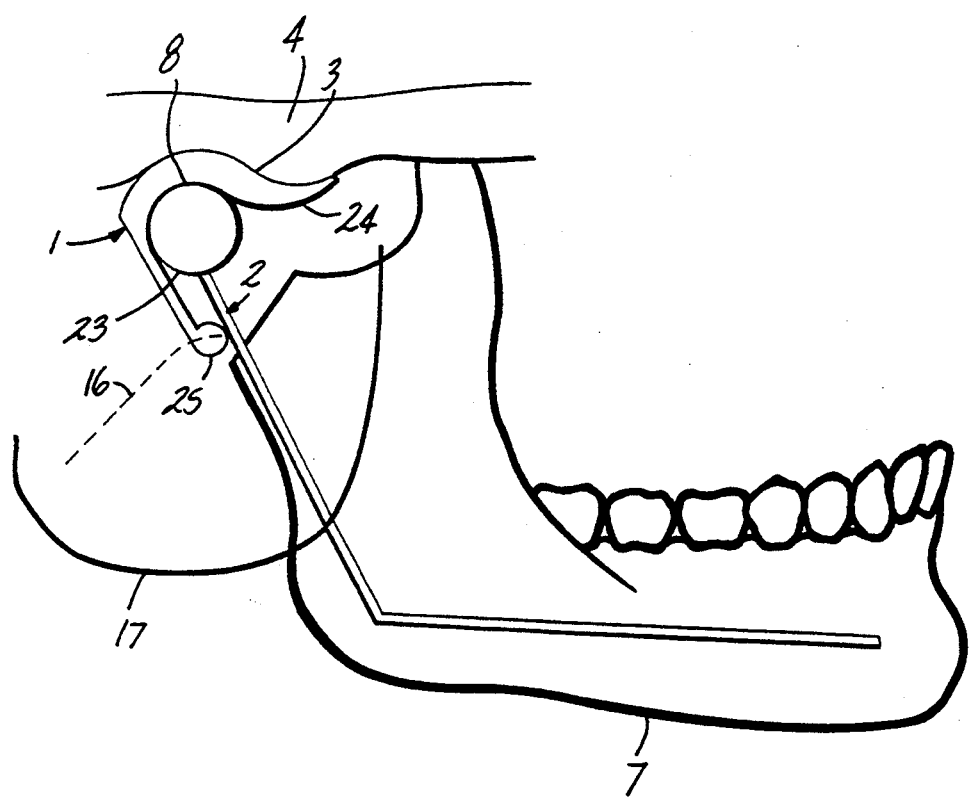
FIG. 5 is a schematical side view of a fourth implanted prosthesis according to the invention.

In FIGS. 3–5 three embodiments of the invention in which the mandibular prosthesis-part 2 is movable relative to the cranial prosthesis-part 1 such that upon rotation of the mandibular prosthesis-part 2, an instantaneous centre of rotation of the mandible moves along a centrode 16. This allows a better fit of the movement of the mandible 7 to the movement of the mandible supported by a natural temporomandibular joint. Research by the applicant has revealed that the centrode of the mandible 7 supported by a natural temporomandibular joint is generally U-shaped, the open side of the path facing upwards, generally as the paths 17 shown in FIGS. 3–5.

The best fit of the mandibular motion with respect to the natural mandibular motion is thus obtained by a prosthesis of which the centrode 16 is U-shaped, the open end of the U-shaped centrode facing towards the cranial prosthesis-part. The centrode 16 of the prosthesis shown in FIG. 3 and, to a lesser extent, the centrode 16 of the prosthesis shown in FIG. 4 have such a shape. Not only the centrodes of movement of the mandibular parts of these prostheses fit very well to the natural corresponding centrodes, also the articulation/translation curves of the mandibular condyles replacing parts fit very well to the natural curves.

As appears from the FIG. 3, a very close fit of the natural and the prosthesis centrodes 17 resp. 16 is obtained if the prosthesis-parts 1 and 2 are connected by two bars 18, 19 hinged between the prosthesis-parts 1 and 2, such that the prosthesis-parts 1, 2 and the bars 18, 19 form a four bar system. If sufficient play is provided in the hinges, the prosthesis also provides the possibility of essentially medial and lateral translational displacement of the prosthesis-parts 1 and 2 relative to each other.

The prosthesis shown in FIG. 4 has a mandibular prosthesis-part 2 comprising an element 20 with a convex bearing surface and a cranial prosthesis-part 1 provided with a bearing surface 21 extending mainly in one direction. The bearing surface 21 is disposed such that in implanted condition the element 20 can slide ventrally and dorsally along the bearing surface 21 of the cranial prosthesis-part 1. Furthermore, an artificial ligament 22 is attached to the element 20 in a position spaced from its bearing surface. Thus a more simple and reliable design, with nevertheless a substantially more natural motion of the mandible 7 is obtained.

The prosthesis shown in FIG. 5 is of a further simplified design, but still allows a substantially more natural movement of the mandible 7 than known temporomandibular prostheses. This is achieved by providing the mandibular prosthesis-part 2 with an element 23 with a convex bearing surface, providing the cranial prosthesis-part 1 with a bearing surface 24 extending mainly in one direction and providing a constraint 25 spaced from and in front of its bearing surface 24 for posteriorly supporting an adjacent part of the mandibular prosthesis-part 2. The bearing surfaces 24 are disposed such that in implanted condition the element 23 can slide ventrally and dorsally along the bearing surface 24 of the cranial prosthesis-part 1.

I claim:

1. A temporomandibular joint prosthesis comprising a cranial prosthesis-part comprising a support surface adapted to be seated against bone tissue in the area of the natural glenoid fossa and the articular eminence and a mandibular prosthesis-part for replacing a natural mandibular condyle having a centre in a position in the glenoid fossa, said mandibular prosthesis-part being adapted to be pivotable about a centre of rotation relative to the cranial prosthesis-part when in implanted condition, said prosthesis-parts comprising bearing surfaces which are curved about the centre of rotation and which mutually fit with a sliding fit, wherein the centre of rotation is located in such a position relative to the support surface of the cranial prosthesis-part, that in implanted condition said centre of rotation is located substantially inferior to said position of the centre of the replaced natural mandibular condyle.

2. A prosthesis according to claim 1, wherein said centre of rotation is located in such a position relative to the support surface of the cranial prosthesis-part, that in implanted condition said centre of rotation is located at least 5 mm inferior to said position of the centre of the replaced natural mandibular condyle.

3. A prosthesis according to claim 1, wherein one of said prosthesis-parts comprises a sphere-shaped cavity and the other one of said prosthesis-parts comprises a sphere-shaped convex element adapted to be seated in said cavity with a sliding fit.

4. A prosthesis according to claim 1, wherein the prosthesis-parts are adapted for translational displacement relative to each other in directions which are essentially medially and laterally oriented when the prosthesis is in implanted condition.

5. A prosthesis according to claim 4, wherein said bearing surfaces are provided in form of a sphere-shaped cavity and a sphere-shaped convex element, and the cranial prosthesis part comprises a traveller movable along a guide in said direction of translational displacement and provided with the sphere-shaped cavity or the sphere-shaped convex element.

6. The prosthesis in accordance with claim 1 wherein said centre of rotation is located inferior to said position of the centre of the replaced natural mandibular condyle by a predetermined distance sufficient to allow translational movement of the prosthesis.

7. A temporomandibular joint prosthesis comprising a cranial prosthesis-part comprising a support surface adapted to be seated against bone tissue in the area of the natural glenoid fossa and the articular eminence and a mandibular prosthesis-part for replacing a natural mandibular condyle having a centre in a position in the glenoid fossa, said mandibular prosthesis-part being adapted to be pivotable relative to the cranial prosthesis-part when in implanted condition, wherein the mandibular prosthesis-part is guided relative to the cranial prosthesis-part such that upon rotation of the mandibular prosthesis-part, an instantaneous centre of rotation of the mandible moves along a centrode comprising a section located substantially inferior to said position of the centre of the replaced natural mandibular condyle.

8. A prosthesis according to claim 7, wherein the centrode is U-shaped, the open end of the U-shaped centrode facing towards the cranial prosthesis-part.

9. A prosthesis according to claim 8, wherein two bars are hinged between said prosthesis-parts, the prosthesis-parts and the bars forming a four bar system.

10. A prosthesis according to claim 7, wherein the mandibular prosthesis-part comprises a convex bearing surface, the cranial prosthesis-part is provided with a bearing surface, the bearing surfaces being disposed such that in implanted condition the element can slide along the bearing surface of the cranial prosthesis-part, and an artificial ligament is attached to the mandibular prosthesis-part at an attachment position spaced from the bearing surface of the mandibular prosthesis part.

11. A prosthesis according to claim 7, wherein the mandibular prosthesis-part comprises a convex bearing surface, the cranial prosthesis-part is provided with a bearing surface and a constraint spaced from the bearing surface of the cranial prosthesis part for supporting an adjacent part of the mandibular prosthesis-part, the bearing surface of the cranial prosthesis part being disposed such that in implanted condition the convex bearing surface can slide along the bearing surface of the cranial prosthesis-part.

12. A cranial prosthesis part for use as part of a total temporomandibular joint prosthesis said prosthesis part comprising a support surface adapted to be seated against bone tissue in the area of the natural glenoid fossa and the articular eminence, a sphere-shaped cavity, the centre defined by said sphere-shaped cavity being located in such a position relative to the support surface, that in implanted condition said centre is located in a plane parallel to and at a distance of at least 11 mm from a central, surface portion of the glenoid fossa.

13. A temporomandibular joint prosthesis comprising a cranial prosthesis-part comprising a support surface adapted to be seated against bone tissue in the area of the natural glenoid fossa and the articular eminence and a mandibular prosthesis-part, said mandibular prosthesis-part being adapted to be pivotable about a centre of rotation relative to the cranial prosthesis-part when in implanted condition, said prosthesis-parts comprising bearing surfaces which are curved about the centre of rotation and which mutually fit with a sliding fit, wherein the centre of rotation is located in such a position relative to the support surface of the cranial prosthesis-part, that in implanted condition said centre of rotation is located in a plane parallel to and at a distance of more than 11 mm from a central surface portion of the glenoid fossa.

14. A prosthesis according to claim 13, wherein the centre of rotation is located in such a position, that in implanted condition it is located in a plane parallel to and at a distance of at least 13 mm from a central surface portion of the glenoid fossa.

* * * * *